United States Patent [19]

Otterbach

[11] 4,129,033

[45] Dec. 12, 1978

[54] SYSTEM FOR DETERMINING THE LEVEL OF HEAT TREATMENT

[76] Inventor: Paul M. Otterbach, 81 E. Coast Dr., Atlantic Beach, Fla. 32233

[21] Appl. No.: 850,263

[22] Filed: Nov. 10, 1977

[51] Int. Cl.$^2$ .......................... G01N 3/20; G01N 3/22
[52] U.S. Cl. ........................................ 73/772; 73/789; 73/837; 73/852
[58] Field of Search .................... 73/15.6, 89, 99, 100, 73/144, 159

[56] References Cited

U.S. PATENT DOCUMENTS

| | | | |
|---|---|---|---|
| 3,158,021 | 11/1964 | Walters | 73/100 |
| 3,196,672 | 7/1965 | Keller | 73/100 |
| 3,708,354 | 2/1973 | Rowell | 73/100 |

*Primary Examiner*—Herbert Goldstein
*Attorney, Agent, or Firm*—George H. Baldwin; Arthur G. Yeager

[57] ABSTRACT

The level of heat treatment of metal strip in a process line is determined by first strain gauge producing a voltage proportional to longitudinal strip tension; selective means deflecting the strip in a lateral direction without materially effecting tension; second strain gauge producing a voltage proportional to lateral force and an amplifier means combining such voltages; setable means coupled to amplifier means output for establishing a predetermined output signal for a specific strip size; means producing voltage proportional to the lateral deflection; means differentiating between a voltage indicative of a gradual strip difference and a voltage resulting from sudden strip deflections; and means combining differentiated signal and latter voltage to produce a combined signal indicative of heat treatment level.

Continuous strip monitoring by strip twisting to cause lateral deflection includes means producing a third voltage proportional to deflection amount and a fourth voltage proportional to strip thickness; and means combining the first and fourth voltages and second and third voltages to produce a combined signal indicative of heat treatment level.

25 Claims, 9 Drawing Figures

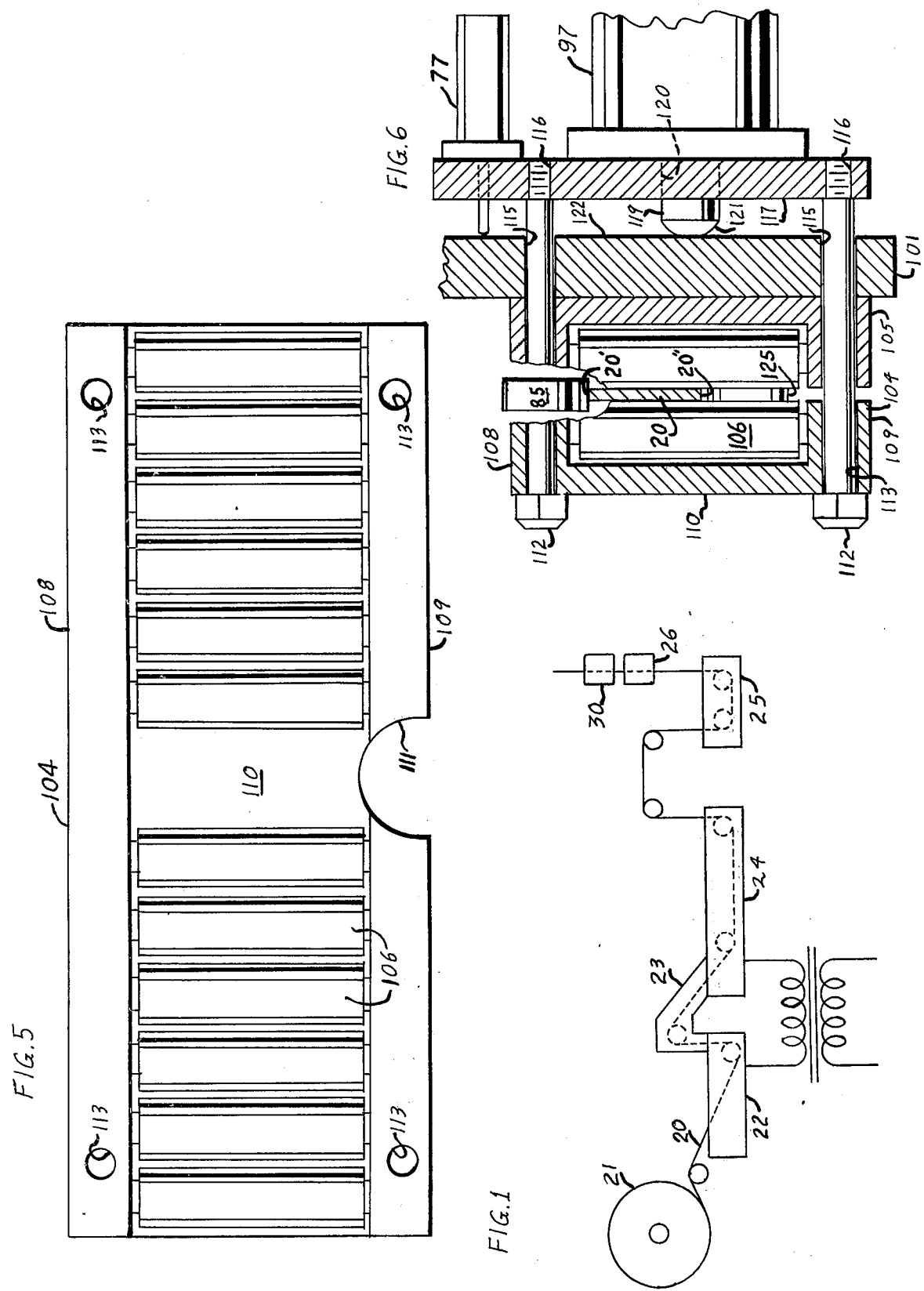

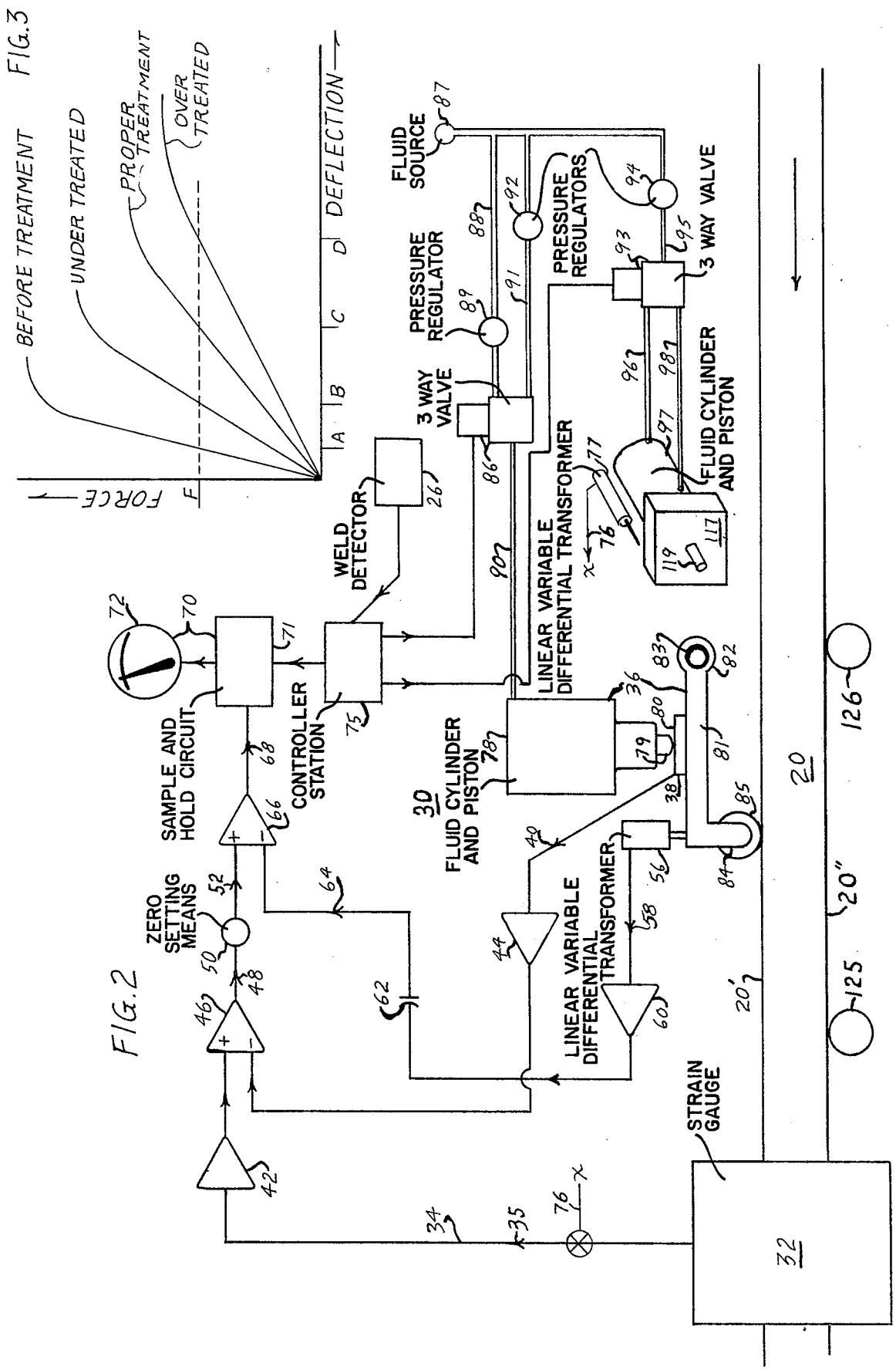

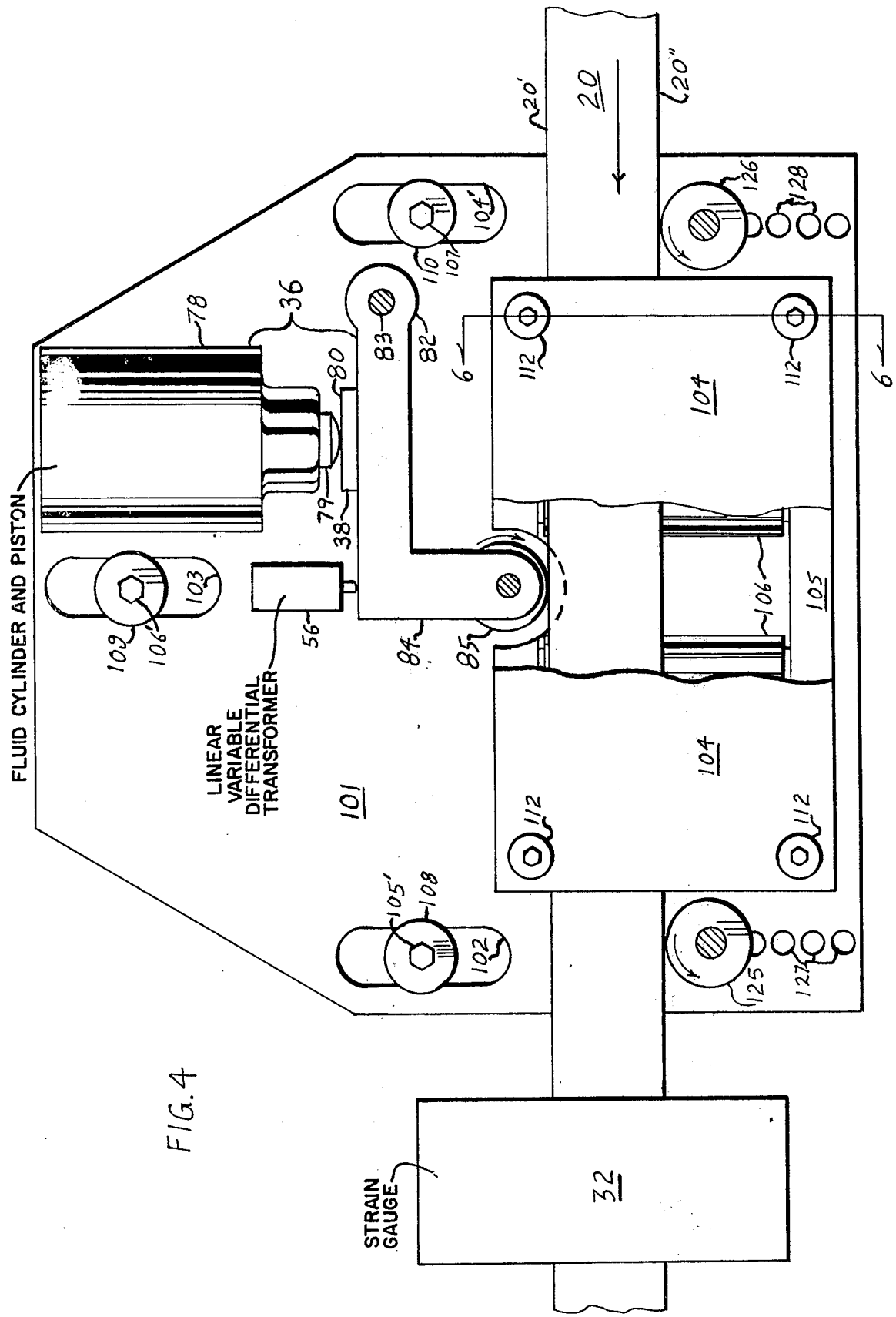

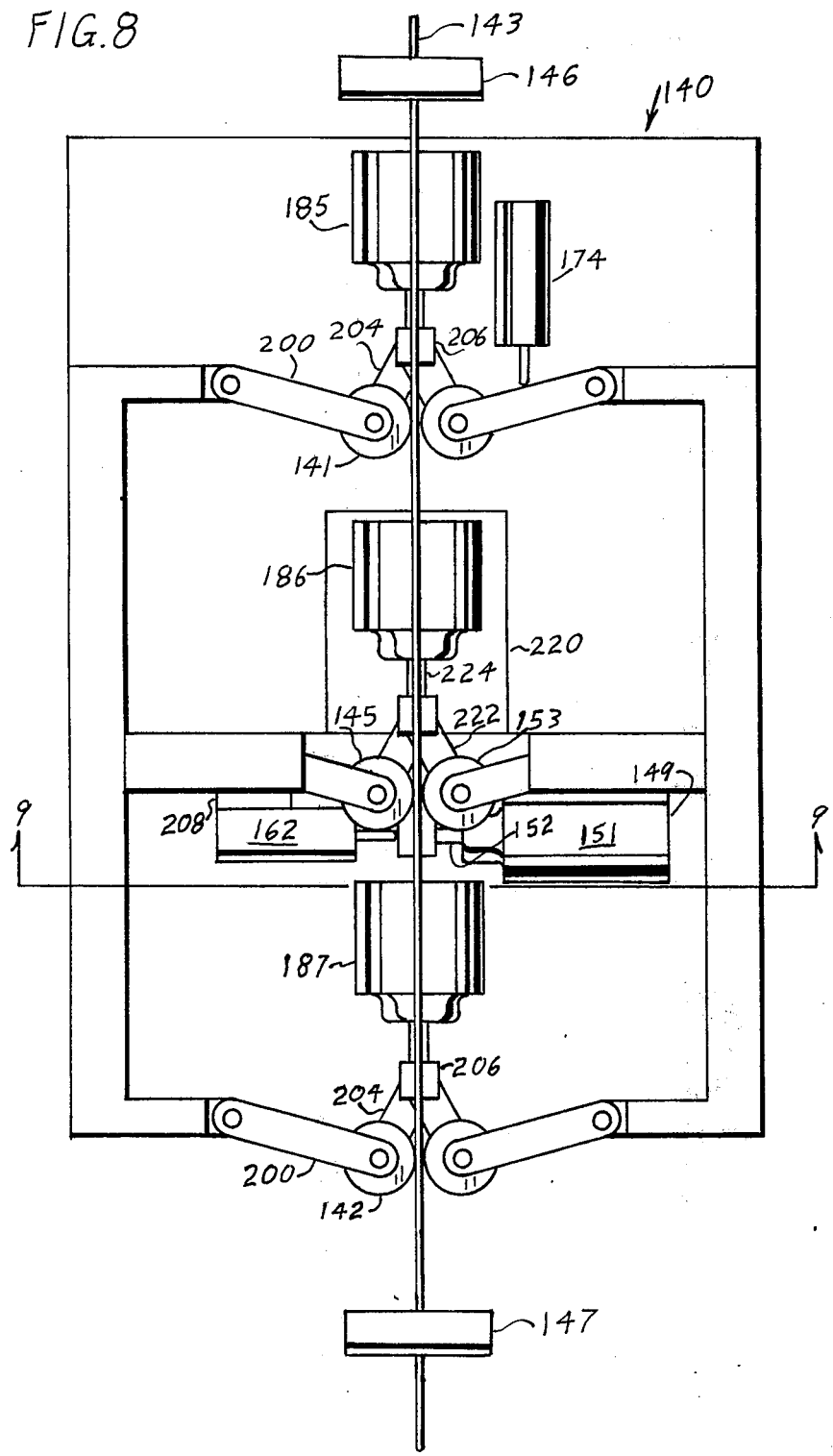

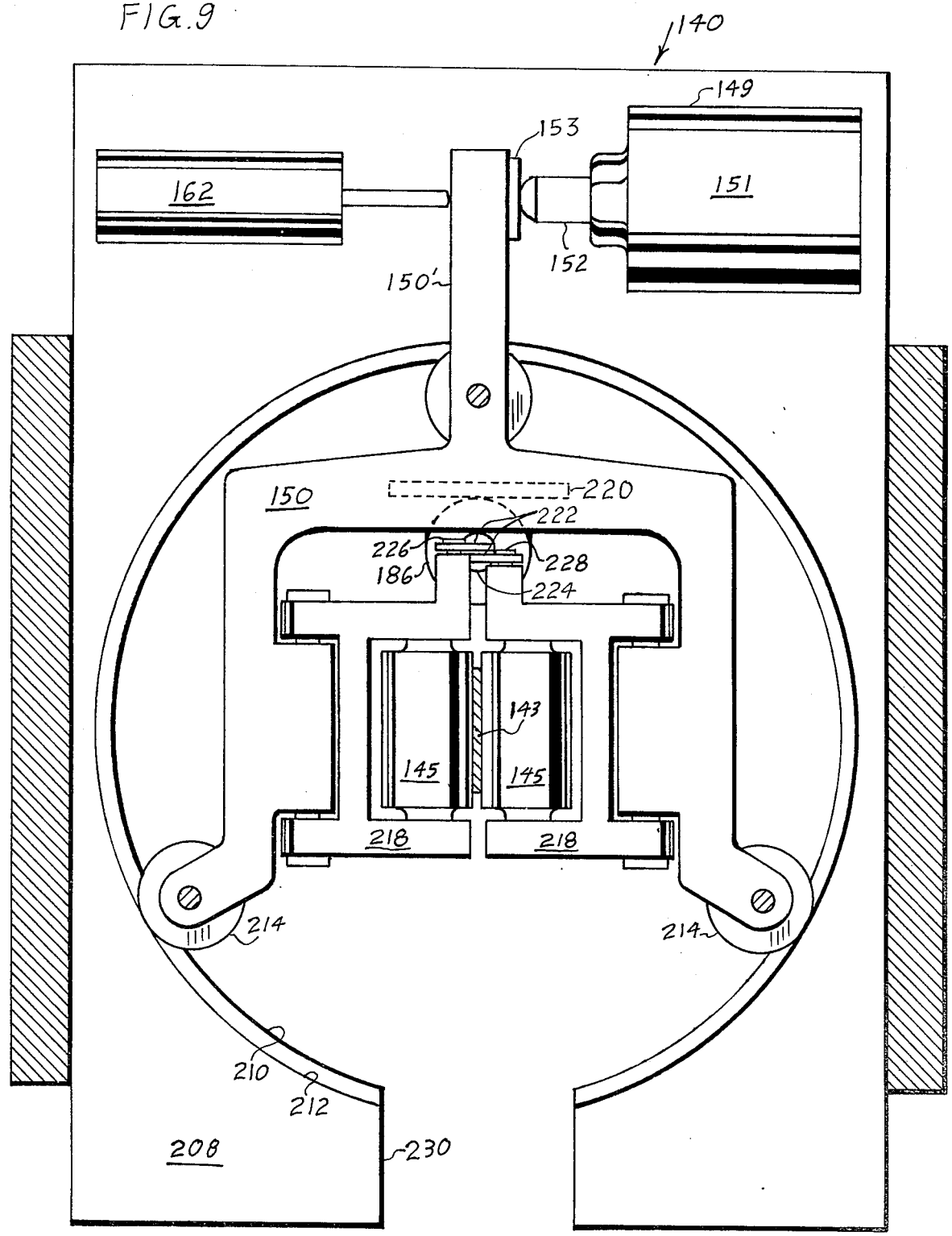

SYSTEM FOR DETERMINING THE LEVEL OF HEAT TREATMENT

DESCRIPTION OF THE PRIOR ART

There are many systems relating to the static or individual sampling of metal strips to determine tension and/or the effectiveness of heat treatment. Illustrative of such systems are those shown in U.S. Pat. Nos. 3,550,427 and 3,206,972. A tension measuring device is shown in U.S. Pat. No. 2,444,245 and such device, which may be considered a strain gauge would be useable as the strain gauge to determine the tension on the moving strip shown in the instant application.

A tension regulator is shown by U.S. Pat. No. 3,447,364 while a sampling and fatigue testing system is disclosed in U.S. Pat. No. 2,729,096. Wavy sheet determining systems are depicted by U.S. Pat. Nos. 2,809,519 and 3,526,114. A system for correcting temperatures and hardness in rolling mills is disclosed in U.S. Pat. No. 3,820,336.

None of the prior art systems disclose a way in which the level of heat treatment can be determined in a continuous process line of metal strip, as with steel banding strips which are heat treated prior to painting, etc. This invention is directed towards alleviating some of the problems encountered in any prior systems, as well as increasing the uniformity of heat treatment of such strips thereby materially reducing the amount of under and over treated reject strips.

SUMMARY OF THE INVENTION

In accord with this invention a system for determining the level of heat treatment of a metal strip under tension in a continuous process line includes a first strain gauge for producing a first voltage proportional to the longitudinal tension of the strip, selective means forceably deflecting the strip in a direction laterally thereof without materially effecting the longitudinal tension, and a second strain gauge for producing a second voltage proportional to the deflecting force. Means are provided to produce a third voltage proportional to the amount of strip deflection, and other means to differentiate between a third voltage produced by any gradual difference in strip size and a third voltage resulting from a sudden forceable deflection of the strip resulting in a differentiated signal. Additional means combine the first and second voltages and the differentiated signal to produce a combined signal indicative of the level of heat treatment of the strip.

Other aspects of the invention include the provision of a first amplifier means for combining the first and second voltages and providing an output voltage, and means coupled to the output of the amplifier means for establishing a predetermined output signal for a specific sized strip. A second amplifier means, into which the output signal and the differentiated signal are supplied, produces the combined signal, and such signal is fed into indicating means for displaying same to an operator. The indicating means includes means for periodically holding the combined signal. In this embodiment of the invention the strip is deflected edgewise of the strip and preferably is intermittently operated.

In accord with another embodiment of the invention the selective means, which forceably deflects the strip in a direction laterally thereof without materially effecting the tension being applied longitudinally thereto, is accomplished in a rotative or twisting manner. In such embodiment, there are provided means for producing a third voltage proportional to the amount of deflection of the strip produced by the selective means, means for producing a fourth voltage proportional to the thickness of the strip, and means for combining such first and fourth voltages and such second and third voltages to produce a combined signal indicative of the level of strip heat treatment. This embodiment is capable of continuously monitoring the level of heat treatment while the edge deflection embodiment is intermittently operated.

A general object of this invention is to provide an improved system for determining the level of heat treatment of a tensioned metal strip in a continuous process line.

A particular object is to provide an intermittent system for monitoring the heat treatment level of a strip.

Another particular object is the provision of a continuous system for monitoring the heat treatment level of a metal strip.

A specific object is to provide a strip edge deflection system to determine the level of heat treatment.

Another specific object is the provision of a twisting deflection system for the strip to determine its heat treatment level.

Other aspects of the invention include an improved system which is economical to and readily constructed, and durable and efficient in use. Upon use of the systems herein disclosed there will be a drammatic reduction in the amount of improper heat treatment of metal strips and the need to store and recycle same, thereby minimizing the use of energy, equipment and labor which will result in tremendous savings to the manufacturer and conservation of resources to the general public.

BRIEF DESCRIPTION OF THE DRAWINGS

The novel features which are believed to be characteristic of this invention are set forth with particularity in the appended claims. The invention itself, however, both as to its organization and method of operation, together with further objects and advantages thereof, may best be understood by reference to the following description taken in connection with the accompanying drawings, in which:

FIG. 1 is a simple diagrammatic sketch of a continuous process line for heat treating metal strip, and incorporating the system in accord with this invention of in line determination of the level of heat treatment so provided;

FIG. 2 is a schematic diagram of one embodiment of the intermittently operable system in accord with this invention;

FIG. 3 is a graphical representation of strip deflection and showing the proper heat treatment curve to be maintained by the operator of the system of FIGS. 1 and 2;

FIG. 4 is a top plan view of the deflecting force portion of the system of FIG. 3;

FIG. 5 is a plan view of one set of identical strip support rollers shown in FIG. 4;

FIG. 6 is a cross sectional view taken along line 6—6 of FIG. 4;

FIG. 8 is a side elevational view of the deflecting force portion of the system of FIG. 7; and FIG. 9 is a cross sectional view taken along line 9—9 of FIG. 8.

DETAILED DESCRIPTION OF THE PREFERRED EMBODIMENTS

Figure 7:
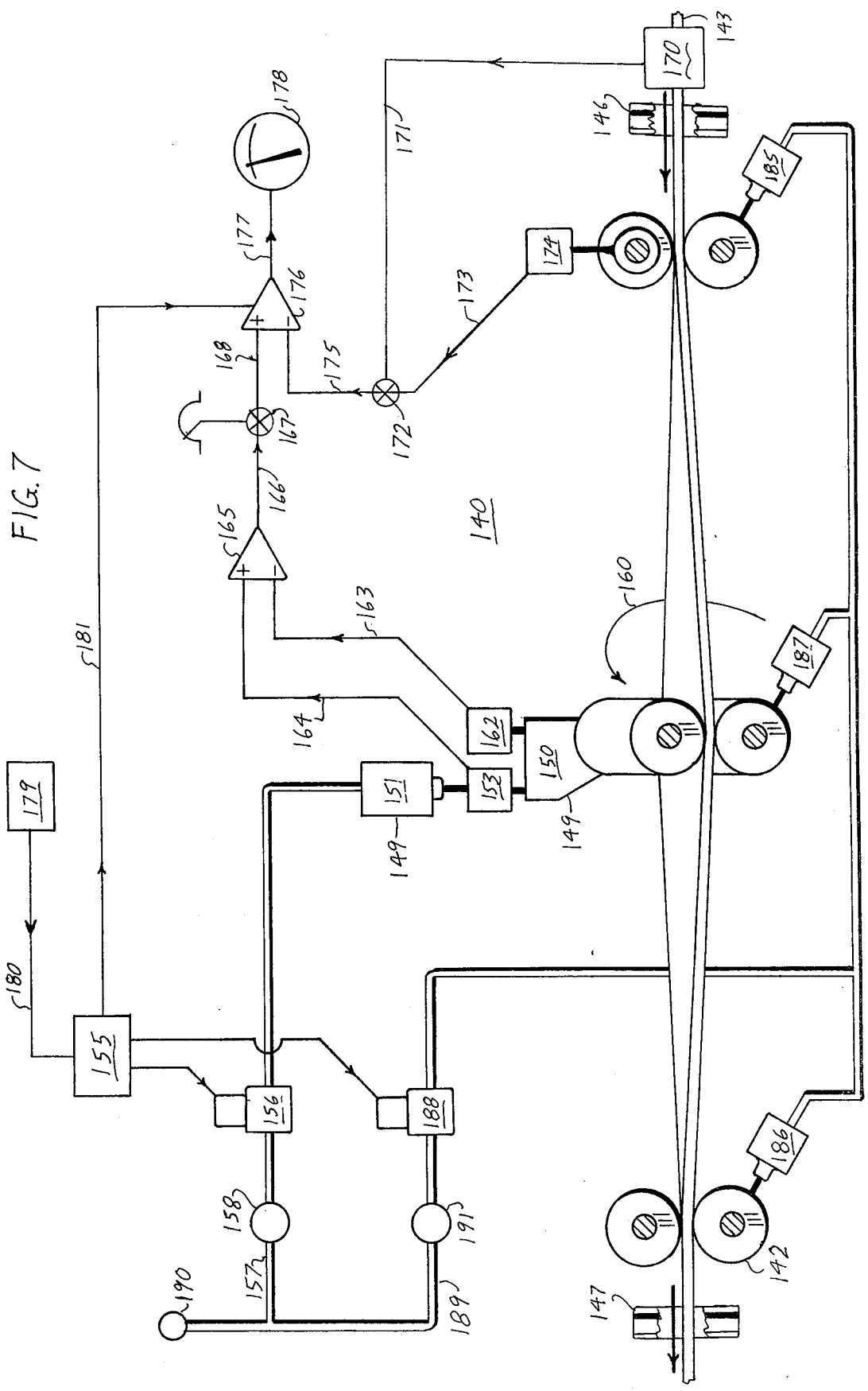
FIG. 7 is a schematic diagram of another embodiment of the system in accord with this invention for in line continuous determination of the level of heat treatment of the strip, with the end rollers spaced a greater distance apart for clarity of illustrating the proper twisting deflection of the strip.

Typically heat treating of steel strips, which generally are from 0.01–0.1 inches thick and 0.5–2.0 inches in width, in continuous process lines is illustrated in FIG. 1 wherein a strip 20 is pulled from a reel 21 at a predetermined rate into a hot lead bath or heating chamber 23, which may be at 800°–900° F.; then into a heating chamber, which may be at 1500°–1700° F.; and then into another hot lead bath 24, which again is at 800°–900° F., such strip being effectively quenched in a manner well known in the art. Thereafter, the strip 20, passes into a cooling water bath 25 through a weld detector 26, through the heat treatment testing station 30, the subject matter of the invention herein disclosed, and then through various other stations including cleaning and painting.

The system for determining the level of heat treatment of a metal strip under tension in a continuous process line is generally indicated by numeral 30 in FIG. 2 and is seen to include a first strain gauge 32 for producing a first voltage 34 proportional to the tension applied longitudinally of the strip 20. Selective means 36 is provided to forceably deflect strip 20 in a direction laterally thereof without materially affecting the tension being applied longitudinally thereto. A second strain gauge 38 produces a second voltage 40 proportional to the force applied to strip 20 by selective means 36. Each of the voltages 34 and 40 are respectively amplified by amplifiers 42 and 44 before they are combined by amplifier 46 for providing an output voltage 48. A zero setting means 50 is coupled to the output of amplifier 46 for establishing a predetermined output signal 52 for a specific strip size. Means, in the form of a linear variable differential transformer (L.V.D.T.), 56 is provided in the system to provide a voltage 58 proportional to the amount of deflection of strip 20 produced by selective means 36, and this voltage 58 is amplified by amplifier 60. Means, in the form of capacitor, 62 provides differentiation between a third voltage indicative of a gradual difference in strip size and a third voltage 64 indicative of a sudden deflection of strip 20 by selective means 36. Means, in the form of an amplifier, 66 combines the output signal 52 and third voltage 64 to produce a combined signal 68 indicative of the level of heat treatment of strip 20.

Thereafter the combined signal 68 is supplied to an indicating means 70 in the form of a sample and hold circuit 71 and a visual indicator 72 wherein the representation of the level of heat treatment is displayed to the operator working the system from controller station 75, in a manner well known in the art.

Since the amount of force required to cause a certain deflection of strip 20 would increase in some proportion to the longitudinal tension being applied to strip 20, the strip tension signal 34 is important to compensate for errors otherwise occurring if such signal were not being used in the herein disclosed system. Also, a thickness measurement signal 76 may be supplied by means, in the form of a L.V.D.T., 77 to a summing point to be added to signal 34 resulting in a combined signal 35 and amplified by amplifier 42. This is important since a thicker strip will require a greater amount of a force to deflect same than a thinner strip, as will be apparent to those skilled in the art.

A single acting fluid cylinder 78 includes a piston rod 79 bearing against a precalibrated pressure pad or plate 80 which is connected to elongated L-shaped lever 81 having end portion 82 pivotal about axis 83 and another end portion 84 rotatably mounting roller 85 in strip edge engagement with strip 20. Thus, when the operator actuates the controls at controller station 75 to open the 3-way solenoid valve 86 pressurized fluid passes through line 88 and pressure regulator 89, via valve 86 and line 90 to force the piston 79 against pressure pad 80 thus moving the edge roller 85 further toward edge 20' to deflect the strip downwardly whereupon the aforementioned voltages and signals are produced and ultimately displayed on the indicator 72, as hereintobefore clearly set forth.

When the valve 86 is deactivated, the pressure within the cylinder 78 and line 90 is allowed to return through line 91 and pressure regulator 92 to the source 87.

In the event that a weld is detected by detector 26, a signal is produced for actuating a four-way solenoid valve 93 which permits fluid to be pumped from source 87 through pressure regulator 94 and line 95, through valve 93 and line 96 to double-acting fluid cylinder 97, hereinafter more fully described. When valve 93 is deactivated, the piston within cylinder 97 is forceably retracted by pressurized fluid from source 87 passing through line 98 below the piston while the fluid above the piston flows out line 96 and valve 93.

The graphical representation of FIG. 3 is illustrative of the strip deflecting forces plotted against the amount of strip deflection occurring by such forces. If the amount of deflecting force being applied is, for example, 200 pounds of force as shown at F, the amount of deflection on the strip material before heat treatment would be, for example, 0.008 inches as shown at A. If the strip is heat treated and the same force F is applied, the amount of deflection would be slightly greater as at B which would be indicative of under heat treatment of the strip. If over heat treatment is provided to the strip in the system of FIG. 1, the amount of its deflection would be substantially greater than the under heat treatment deflection at B, as is depicted at D. The amount of deflection for proper heat treatment as related to the same deflecting force being applied to the strip is shown at C. The amount of deflection on this graph is illustrative only and the horizontal scale has been expanded for clarity.

Thus the operator performing periodic in line testing of the level of heat treatment, as disclosed in FIGS. 1 and 2, can obtain appropriate readings from indicator 72, and with the knowledge of the approximate amount of deflection for a particular size and type of strip, the operator will emprically know whether the strip is being properly heat treated, i.e., if the readings do not correspond to the approximate and proper C deflection obtained the operator can then vary the temperatures of the baths 22 and/or 24 and/or heating chamber 23 and/or the cooling bath 25 or take other appropriate corrective measures.

The deflecting force portion 100 of the system 30 is shown in FIGS. 4, 5 and 6 and is seen to include a frame 101 moveably mounted by means, such means comprising a three elongated spaced slots 102, 103 and 104' having their axes extending parallel and laterally of strip 20 and fixed supports 105', 106' and 107 onto which are disposed rollers 108, 109 and 110 engaging respective slots 102, 103 and 104' whereby the frame 101, together with the other components mounted thereto, may laterally wander with the strip 20 in a manner well known in the art.

Two sets of support rollers 104 and 105 sandwich strip 20 therebetween and each of the sets of rollers 104 and 105 is identical and is clearly seen in FIG. 5. Rollers 106 are parallel and are suitably journalled at their respective ends into parallel supports 108 and 109 which may be unitarily joined by back plate 110. A cut-out 111 is provided in each of the supports 109 to accomodate the deflecting roller 85 which bears against the upper edge 20' of strip 20 as clearly illustrated in FIGS. 4 and 6.

Four bolts 112 pass through straight elongated passageways 113 in each of the sets of rollers 104 and 105 and through aligned passageways 115 in frame 101 terminating in threaded connections, as at 116, in cylinder supporting plate 117 spaced away from frame 101. Plate 117 supports double acting weld relieving fluid cylinder 97 thereon with its piston 119 passing through an opening 120, shown in broken lines in FIG. 6, and its end 121 engaged against frame surface 122. Thus, it is seen that the sets of rollers 104 and 105 are slideably supported by spaced and parallel support bolts 112 so that when a weld of the strip 20 is approaching the heat treatment determining station 30, cylinder 97 retracts its piston 119 so that roller set 105 may move away from roller set 104 to permit the enlarged weld of strip 20 to pass therethrough.

Since roller 85 is engaged with edge 20' of strip 20, means in the form of a pair of spaced rollers 125 and 126 are in contact with strip edge 20" and provide edge wise support so that the entire strip will not simply move over during the time when a deflecting force is applied through roller 85. A plurality of laterally spaced openings 127 and 128 are provided so that respective rollers 125 and 126 may be repositioned to accommodate various widths of strip material passing through the heat level system or station 30.

In summary, the system operates as follows:

I. Strip 20 passes through and is contained within two facing sets of rollers 104 and 105 which prevent any buckling thereof. The rollers engage the flat surfaces of the strip 20 and are separatably mounted so that an abnormal thickness of strip, such as a weld, may pass therebetween.

II. Two rollers contact one edge 20" of the strip 20 and are spaced apart about six inches and the deflecting roller 85 is located midway between but against the opposite edge 20' of strip 20, roller 85 is mounted so that it is free to move against the strip edge 20' and has attached to it, a means 78 for forcing it against the strip, a means 80 for measuring the amount of force exerted and a means 56 for measuring the amount of deflection being caused by the force exerted against strip 20. The amount of force and the amount of deflection are translated into electrical quantities by, for example, a strain gauge and linear variable differential transformer (L.V.D.T.).

III. The signal from the force measuring strain gauge 80 and the signal from a tension measuring strain gauge 32 are amplified by amplifiers 42 and 44. These two signals are combined by a differential operational amplifier 46, since higher strip tension will require a higher deflecting force to achieve the same amount of deflection. The output of amplifier 46 is modified by an addition of a zero setting device 50 used to set up the system for a specific strip size. This conditioned signal thus represents the deflecting force being applied to the strip 20.

IV. This conditioned force signal is compared with a signal proportional to the amount of deflection caused by the deflecting force. The deflectional signal is conditioned prior to such comparison. The roller 85 contacting the edge 20' of the strip, as well as the rollers 125 and 126 in contact with strip edge 20" determine and measure strip width as well as deflection, so a means is provided in the electronics to continually compensate for width variations. When the strip is not under tension, the three edge rollers 85, 125 and 126 are held in contact with the edges 20' and 20" of the strip 20 by a very low force. During this time the system is sensing the width of strip 20 and the signal from the deflection transducer pad 80 will reflect any change in width. Amplifier 60 which conditions this signal, drives amplifier 66 through a capacitor 62 selected to differentiate between gradual changes in strip width and the larger, more sudden change in signal which occurs when a much higher level of force is applied for deflecting the strip 20 during a test. This higher force may be applied for about one second and then reduced to the level required to maintain contact of the edge rollers 85, 125 and 126 to the strip.

V. During the period of higher deflecting force, the signals from the strain gauges 32 and 80 are combined into the final heat treatment signal and stored by a sample and hold circuit 71 with the output therefrom being connected to the meter indicator 72 thus providing time for the process operator to note the readings.

VI. The device applies the same force during each test and the amount of deflection is then a measure of the level of heat treatment of the strip under test. The final heat treatment readings can be used as an indication to the process operator as data for quality control or may be employed as an input to a process control system to permit automatic in line compensation of the heat reatment system.

Another embodiment of the system for determining the level of heat treatment of a metal strip under tension is depicted in FIG. 7 and generally indicated by numeral 140. Such a system comprises a pair of spaced and aligned sets of rollers 141 and 142 with the strip 143 passing through each roller set and being supported thereby. Another set of rollers 145, in its inoperative position, permits the strip to pass therebetween without any deflecting forces being applied to the strip. Side edge sets of rollers 146 and 147 are engaged against the side edges of the strip at the respective entrance and exit of the strip 143, as illustrated in FIGS. 7 and 8, to prevent lateral shifting thereof during the deflection of the strip 143 applied by operation of the set of rollers 145, as hereinafter more fully described.

Basically, this system 140 differs from system 30, hereinbefore described in connection with FIGS. 1-6, in that the deflection of the strip 143 is in a twisting or rotating manner as compared to the edge or lateral bending of the strip 20 in the first embodiment of the invention. The twisting of the rollers 145 and the general mechanical arrangement of the components are depicted in FIG. 9 and will be described hereinafter. Suffice to say that the rollers 145 which are mounted to selective means 149 to forceably deflect strip 143 includes a movable frame 150, such frame being powered by single acting fluid cylinder 151 having a piston rod 152 bearing against a strain gauge in the form of precalibrated pressure pad, load cell or plate 153 which is coupled to frame 150. When the operator actuates the controls in the controller station 155 to open 2-way solenoid valve 156, pressurized fluid passes through line 157 and pressure regulator 158, via valve 156 and line 159 to force the piston 152 of cylinder 151 against pressure pad 153 thus moving the frame 150 and the rollers 145 carried thereby in a pivotal, rotatable, or twisting direction, as illustrated by arrow 160, to deflect the strip 143 from its planar state into a twisted state, whereupon means 162, in the form of L.V.D.T., detects the amount of deflection of strip 143 and provides a voltage 163 proportional to the amount of deflection produced by selective means 149. Also, the load cell 153 produces a voltage 164 proportional to the force being applied to strip 143 by the selective means 149. Means in the form of an amplifier 165 combines the signal 166 therefrom which is fed through a zero setting means 167 for establishing a predetermined output signal 168 for a specific strip 143 being passed in the system.

A strain gauge 170 produces a voltage 171 proportional to the longitudinal tensioning of strip 143 which is fed to a summing point 172 to be added to signal 173, such signal being produced by means, in the form of a L.V.D.T., 174 which coacts with rollers 141 to produce a signal proportional to the thickness of strip 143. The combined signal 175 is combined and amplified by amplifier means 176 to produce a combined output signal 177, indicative of the level of heat treatment applied to strip 143, which may be displayed by indicating means 178 to the operator in the controller station 155 on a virtually continuous basis. This feature points to one of the several advantages of this embodiment, namely the generally continuous monitoring of the level of heat treatment, as compared to the intermittent and sample and hold operation, and the independence from the unevenness or undulations of the edges of the strip. Of course, both embodiments operate at deflecting force levels well below the yield strength of the strip to assure that the deformations being applied are only temporary and no permanent deformation of the strip will occur by operation of either embodiment of the invention.

In the event that a weld is encountered by weld detector 179, a signal 180 is produced to nullify the output signal 177 from amplifier 176, as illustrated by line 181. While the weld detector 179 is shown in this embodiment of the invention it is possible to omit same, since the sets of rollers 141, 142 and 145 will permit the ingress of a weld therethrough, as will be hereinafter more fully described.

At least one roller 141', 142', and 145' of respective sets of rollers 141, 142 and 145 is movably supported with respect to the other roller of each set and such rollers are actuated by corresponding single acting fluid cylinders 185, 185 and 187 which are controlled through 2-way solenoid valve 188 by the operator. Pressurized fluid is passed through concuit 189 from the source 190, via regulator 191 and valve 188 to each of the cylinders 185, 186 and 187 so that the strip may be firmly engaged by each of the sets of rollers 141, 142 and 145 prior to and during the twisting of the strip by roller set 145.

Considering FIGS. 8 and 9 in greater detail it is seen that each roller of sets 141 and 142 is rotatably mounted at the free end of an arm 200 with the opposite end thereof being mounted to stationary frame 202 of the apparatus. Also, a link 204 communicates between and is pivotally connected to roller arm 200 and affixed to piston end 206 of fluid piston and cylinder assemblies 185 and 187. Thus, when cylinders 185 and 187 are actuated, the pistons of assemblies 185 and 187 retract, pulling links 204 and causing rollers of each set 141 and 142 to move closer together to firmly grip the strip 143 passing between rollers of each such set. If a weld passes between the rollers, the rollers merely move apart sufficiently to permit the passage of such weld.

Cylinder 151 and the L.V.D.T. are mounted to an upstanding plate 208 which is suitably connected to main frame 202. Plate 208 has an enlarged opening 210 therethrough which may include a track or a groove 212 in which a plurality of rollers 214 may ride. Rotatable or twistable frame 150 is connected to rollers 214 so that the frame 150 may rotate about the longitudinal axis of the strip 143 when cylinder 151 is actuated. Frame 150 includes a lever 150' extending upwardly, as seen in FIG. 9 onto which pad 153 is mounted on the right side thereof for engagement by piston rod 152 of fluid cylinder 151, with L.V.D.T. engaging the other side of lever 150'. Frame 150 is seen to be generally U-shaped and includes a pair of lugs 216 for pivotally attaching roller supports 218 which are bifurcated and in turn rotatably connect rollers 145 thereof. Carried with and supported by frame 150 is support member 220 to which fluid cylinder 186 is attached. Links 222 extend between the piston rod 224 and their pivotal connections at 226 and 228 with roller supports 218. Each of the arms 200 may be substantially indentical to bifurcated roller supports 218, as would be apparent to those skilled in the art.

The slot 230 communicates between opening 210 and externally of the frame plate 208 so that the strip may be properly positioned between rollers 145. As may be seen, only a small degree of twisting is envisioned for the strip 143 and thus the slot 230 would not be encountered by either of the two rollers 214. When cylinder 151 is actuated, rod 152 bears against pad 153 moving lever 150' and frame 150 counterclockwise to cause twisting of strip 143 caged between rollers 145.

In summary, it will be seen that two pairs of rollers 141 and 142 are provided to support the strip 143 and a third pair of rollers 145, located centrally between the supporting rollers 141 and 142, are mounted so as to be free to rotate about the center line of motion of strip 143. All three sets of rollers 141, 142 and 145 include means for holding the rollers firmly against strip 143 while permitting seperation of the strip during start-up of the process line or during the passage of a weld.

The movable mounting frame 150 of the rollers 145 is actuated by means 149 for moving the frame 150 and rollers 145 to rotate about the centerline of motion of strip 143. Another means 162 measures the angle to which the frame 150 has rotated about the centerline of motion of the strip. Also a linear variable differential transformer 174 is attached to one of the sets of rollers 141, 142 or 145 to provide a signal proportional to thickness of strip 143.

As in the first embodiment the same basic relationship of force to deflection as an indication of the level of heat treatment applies. The primary difference in the system is that the lateral deflection is in the manner of a twist of the strip instead of a linear force applied to the strip as an edge or beam deflection. The system basically operates as follows:

The signal representing a twisting deflection is provided by L.V.D.T. 162 and the signal representing the deflecting force is provided by a strain gauge 153 located in the mechanical path of the force from a cylinder 151. These two signals are combined in the differential operational amplifier 165 to provide a signal 168 proportional to the level of heat treatment of the strip 143. This output signal 168 is then combined with a signal 175 representing the strip thickness by a differential operational amplifier 176, thus, minimizing error due to variation in strip thickness.

While the invention has been described with respect to certain specific embodiments, it will be appreciated that many modifications and changes may be made by those skilled in the art without departing from the spirit of the invention. It is intended, therefore, by the appended claims to cover all such modifications and change as fall within the true spirit and scope of the invention.

What is claimed as new and what is desired to secure by Letters Patent of the United States is:

1. In a system for determining the level of heat treatment of a metal strip under tension in a continuous process line comprising a first strain gauge for producing a first voltage proportional to the tension applied longitudinally of said strip, selective means for forceably deflecting said strip in a direction laterally of said strip without materially effecting the tension being applied longitudinally to said strip, a second strain gauge for producing a second voltage proportional to the force applied to said strip by said selective means, means for producing a third voltage proportional to the amount of deflection of said strip produced by said selective means, means for differentiating between a said third voltage produced by a gradual difference in strip size and a said third voltage resulting from a sudden deflection of said strip by said selective means for providing a differentiated signal, means for combining said first and second voltages and said differentiated signal to produce a combined signal indicative of the level of heat treatment of said strip.

2. In the system as defined in claim 1 wherein said means for combining said first and second voltages and said differentiated signal comprises a first amplifier means for combining said first and second voltages and providing an output voltage, and means coupled to the output of said amplifier means for establishing a predetermined output signal for a specific strip size.

3. In the system as defined in claim 2 wherein said means for combining includes a second amplifier means into which said output signal and said differentiated signal are supplied and producing said combined signal and displaying same to an operator.

4. In the system as defined in claim 3 wherein said indicating means includes means for periodically holding said combined signal.

5. In the system as defined in claim 1 further comprising indicating means for receiving and displaying said combined signal to an operator.

6. In the system as defined in claim 5 wherein said indicating means includes means for periodically holding said combined signal.

7. In the system as defined in claim 1 wherein said selective means provides an edge displacement of said strip.

8. In the system as defined in claim 1 wherein said strip includes flat surfaces and a pair of side edges said system further comprising, a frame, a pair of sets of rollers mounted to said frame and respectively engaging said strip flat surfaces, one of said sets of rollers being movably mounted with respect to the other of said sets of rollers whereby an increased thickness of strip may pass between said sets of rollers, a pair of spaced rollers rotatably mounted to said frame on respective sides of said sets of rollers and engaging one of said strip side edges, said selective means including a roller and means for movably mounting said roller to said frame with said roller engaging the other of said strip side edges generally medially of said pair of spaced rollers, said selective means further including power means maintaining said roller in engagement with its said other strip side edge and being operable to forceably deflect said strip in a direction laterally thereof, said sets of rollers caging said strip therebetween to inhibit other spurious motion of said strip.

9. In the system as defined in claim 8 further comprising a stationary support, mounting means connected between said support and said frame to mount said frame for movement laterally of said strip.

10. In the system as defined in claim 8, wherein said means for moveably mounting said roller includes an elongated arm pivotally connected to said frame one of its ends carrying said roller at its other end, said power means applying its forces through said arm to said roller.

11. In the system as defined in claim 8 wherein said roller is located generally medially of said sets of rollers.

12. In the system as defined in claim 8 further comprising actuatable means for forceably moving said moveable one set of rollers toward and away from said other said of rollers thereby respectively tightly gripping and releasing said strip therebetween.

13. In the system as defined in claim 8 wherein said pair of rollers are releaseably attached at various lateral positions to accommodate various widths of strips between said pair of rollers and said roller.

14. In a system for determining the level of heat treatment of a metal strip under tension in a continuous process line comprising a first strain gauge for producing a first voltage proportional to the tension applied longitudinally of said strip, selective means for forceably deflecting said strip in a direction laterally of said strip without materially effecting the tension being applied longitudinally to said strip, a second strain gauge for producing a second voltage proportional to the force applied to said strip by said selective means, means for producing a third voltage proportional to the amount of deflection of said strip produced by said selective means, means for producing a fourth voltage proportional to the thickness of said strip, and means for combining said first and fourth voltages and said second and third voltages to produce a combined signal indicative of the level of heat treatment of said strip.

15. In the system as defined in claim 14 wherein said means for combining said first and fourth voltages and said second and and third voltages comprises a first amplifier means for combining said first and fourth voltages and providing an output voltage, a second amplifier means for receiving said second and third voltages and combining same with said output voltage, and means coupled to the output of said second amplifier means for establishing a predetermined output signal for a specific strip size.

16. In the system as defined in claim 15 further comprising indicating means for receiving said output signal from said second amplifier means and displaying same to an operator.

17. In the system as defined in claim 16 wherein said indicating means continuously monitors the level of heat treatment being applied to said strip.

18. In the system as defined in claim 14 further comprising indicating means for receiving said combined signal, said indicating means continuously monitoring the level of heat treatment being applied to said strip.

19. In the system as defined in claim 14 wherein said selective means provides a twising movement to said strip.

20. In the system as defined in claim 14 further comprising, a frame, a pair of spaced sets of rollers mounted to said frame and a roller of each set engaging one of the flat surfaces of said strip and other roller of each set engaging the other flat surface of said strip, said rollers of each set being moveably mounted with respect to each other whereby an increased thickness of strip may pass between said rollers of each set, a pair of rollers rotatably mounted to said frame and respectively engageable with said strip faces, said selective means being connected to said pair of rollers to rotate same to angularly deflect said strip.

21. In the system as defined in claim 20 further comprising a moveable frame, means for moveably mounting said pair of rollers to said moveable frame, said moveable frame being rotatably mounted to said frame, said selective means including power means operable to forceably and angularly deflect said strip in a direction laterally thereof, said sets of rollers caging said strip therebetween to inhibit other spurious motion of said strip.

22. In the system as defined in claim 20 further comprising means for biasing said pair of spaced sets of rollers and said pair of rollers toward said strip.

23. In the system as defined in claim 22 wherein said means for biasing includes a power means for each of said pair of rollers.

24. In the system as defined in claim 20 further comprising means for moveably mounting said moveable frame to said frame which includes a U-shaped support member having a plurality of wheels, said frame having a groove in which said wheels are cages, said power means applying its forces through said U-shaped support member to said pair of rollers.

25. In the system as defined in claim 20 further comprising actuatable means for forceably moving said rollers of each pair of rollers toward and away from each other thereby respectively tightly gripping and releasing said strip traveling therebetween and therethrough.

* * * * *